(12) United States Patent
Wiederkehr et al.

(10) Patent No.: US 11,399,879 B2
(45) Date of Patent: Aug. 2, 2022

(54) DEVICES AND METHODS FOR POSITIONING OF AN IMPLANT

(71) Applicant: Stryker European Operations Holdings, LLC, Wilmington, DE (US)

(72) Inventors: Andreas Wiederkehr, Biel/Bienne (CH); Katja Stucki, Lenzburg (CH); Matthias Paulisch, Roggwil (CH); Alex Trompeter, Surrey (GB)

(73) Assignee: Stryker European Operations Holdings, LLC, Wilmington, DE (US)

( * ) Notice: Subject to any disclaimer, the term of this patent is extended or adjusted under 35 U.S.C. 154(b) by 244 days.

(21) Appl. No.: 16/441,711

(22) Filed: Jun. 14, 2019

(65) Prior Publication Data

US 2019/0380753 A1 Dec. 19, 2019

Related U.S. Application Data

(60) Provisional application No. 62/685,465, filed on Jun. 15, 2018.

(51) Int. Cl.
*A61B 17/80* (2006.01)
*A61B 17/88* (2006.01)
*A61B 17/29* (2006.01)
*A61B 17/28* (2006.01)
*A47G 25/06* (2006.01)
(Continued)

(52) U.S. Cl.
CPC ........ *A61B 17/808* (2013.01); *A61B 17/8061* (2013.01); *A47G 25/0628* (2013.01); *A47G 29/083* (2013.01); *A61B 17/28* (2013.01); *A61B 17/282* (2013.01); *A61B 17/8866* (2013.01); *A61B 2017/2904* (2013.01);
(Continued)

(58) Field of Classification Search
CPC . A61B 17/808; A61B 17/8061; A61B 17/886; A61B 17/28; A61B 17/282; A61B 17/2812; A61B 2017/2904; A61B 2017/2926; A61B 2017/2945; A47G 25/0607; A47G 25/32; A47G 25/08; A47G 25/0614; A47G 25/0621; A47G 25/0628; A47G 25/0635; A47G 25/10; A47G 29/083; A47B 53/02; Y10T 24/32; F21V 21/088; F16L 3/1218; F16L 3/02; F16G 11/00
USPC ......................................... 606/324, 205, 281
See application file for complete search history.

(56) References Cited

U.S. PATENT DOCUMENTS 4,953,817 A * 9/1990 Mosteller ................ A47F 5/083
24/686
D343,521 S * 1/1994 Wigley, Sr. .................... 294/137
(Continued)

OTHER PUBLICATIONS

Trompeter et al., "Assisting the positioning of the proxinal portion of percutaneous anterolateral distal tibial periarticular plates", The Annals of the Royal College of Surgeons of England, Apr. 2013; 95: 222-227.

*Primary Examiner* — Marcela I. Shirsat
(74) *Attorney, Agent, or Firm* — Lerner, David, Littenberg, Krumholz & Mentlik, LLP (57) ABSTRACT

A device for positioning a bone plate includes a body having a first end having a first curved portion and a second end having a second curved portion. Each curved portion terminates at an abutment. Each abutment has a first diameter and the curved portions have a second diameter less than the first diameter. The first end secures the positioning device to a bone plate and the second end secures the positioning device to a soft tissue elevator.

19 Claims, 5 Drawing Sheets

FIG. 6

(51) Int. Cl.
*F21V 21/088* (2006.01)
*A47G 29/08* (2006.01)

(52) U.S. Cl.
CPC ............... *A61B 2017/2926* (2013.01); *A61B 2017/2945* (2013.01); *F21V 21/088* (2013.01)

(56) References Cited

U.S. PATENT DOCUMENTS

| | | | |
|---|---|---|---|
| 5,578,032 A * | 11/1996 | Lalonde | A61B 17/282 606/205 |
| 7,648,508 B2 | 1/2010 | Lutz et al. | |
| 8,398,637 B2 | 3/2013 | Parsell et al. | |
| 2006/0149315 A1 * | 7/2006 | Kebel | A61B 17/28 606/205 |
| 2010/0152789 A1 * | 6/2010 | Dell'Oca | A61B 17/8866 606/324 |
| 2012/0198680 A1 * | 8/2012 | Durben | F16L 3/1218 29/428 |
| 2013/0037672 A1 * | 2/2013 | Sanchez | B60R 7/10 248/303 |
| 2018/0135729 A1 * | 5/2018 | Shen | A47J 45/02 |

* cited by examiner

FIG. 13

# DEVICES AND METHODS FOR POSITIONING OF AN IMPLANT

CROSS-REFERENCE TO RELATED APPLICATIONS

This application claims the benefit of the filing date of U.S. Provisional Patent Application No. 62/685,465, filed on Jun. 15, 2018, the disclosure of which is hereby incorporated by reference herein.

BACKGROUND OF THE INVENTION

The present disclosure relates generally to devices and methods for positioning implants on bone, and more particularly, for positioning plates on bones.

In minimally invasive surgery of bones, such as the femur, it can be difficult to correctly place the implant, such as a plate, along and/or in the bone. In such a surgery, a proximal and a distal incision are made to enable access to the bone. Typically, the plate is inserted through one of the incisions and pushed subcutaneously toward the other incision. However, due to the long distance between the proximal and distal incisions, it can be difficult for a surgeon to control the positioning, e.g. direction and rotation, of the plate. Typically, a long lever arm forms between the tip of the plate, which pushes at the soft tissue, and the inserter handle at the other end. As a result, small, involuntary changes of angulation of the inserter can lead to significant misguiding of the plate. Moreover, the use of pre-contoured plates in a bone can pose particular challenges for placement. For instance, if the ends of the plate are pre-contoured away from the bone, and thus not flat, it can be difficult to maintain the plate on the bone surface as pushing the plate can cause the end to move upward away from the bone.

Thus, there is a need for more precise control and placement of implants within bones in minimally invasive approaches.

BRIEF SUMMARY OF THE INVENTION

A positioning device may be used to place a bone plate in its correct position on a bone. Generally, the method may include forming a canal by clearing out the soft tissue with a soft tissue elevator and then attaching a first end of the device to the soft tissue elevator and attaching the second end of the device to a plate. The soft tissue elevator, device, and plate are then pulled along the bone to a second incision spaced apart from the first incision where the elevator and device are removed and the plate positioned. This reduces the number of steps in the method.

A first aspect of the present disclosure is a device for positioning an implant, such as a bone plate. The device includes a body that has a first end that has a first curved portion and a second end that has a second curved portion, each curved portion terminates at an abutment. The abutment has a first diameter and the curved portions have a second diameter less than the first diameter.

In other embodiments, second end may have two second curved portions spaced apart from each other. An abutment edge may be positioned between each curved portion and each abutment. The abutments may be shaped as at least part of a sphere. The device may be substantially rigid.

A second aspect of the present disclosure is a system for positioning an implant, such as a bone plate, on a bone. The system includes a soft tissue elevator for clearing soft tissue in a canal of the bone, a bone plate, and a device for positioning the plate. The device has a first end that has a first curved portion and a second end that has two second curved portions. The device is attachable at the first end to the bone plate and at the second end to the soft tissue elevator.

In other embodiments, each curved portion may terminate at an abutment. The abutment at the first end may be sized and shaped to fit within a hole of the bone plate, and the abutments at the second end may be sized and shaped to fit within an opening of the soft tissue elevator. The abutment at the first end may have a first diameter and the curved portions may have a second diameter less than the first diameter. The hole of the plate may have a third diameter greater than each of the first and second diameters. The first curved portion may have an inner blocking surface that prevents upward movement of a tip of the bone plate, when the abutment is positioned within the hole of the plate. The two second curved portions of the second end may conjoin to form the first curved portion of the first end.

A third aspect of the present disclosure is a method of positioning an implant, such as a bone plate. The method includes inserting a soft tissue elevator into a first incision, moving the soft tissue elevator in a first direction along the bone to a second incision, attaching a first end of a positioning device to a bone plate, attaching a second end, opposite the first end, of the positioning device to the soft tissue elevator, and pulling the soft tissue elevator in a second direction, opposite the first direction, such that the positioning and the bone plate are also pulled in the second direction.

In other embodiments, the method may include attaching the bone plate by attaching a first abutment of a first curved portion of the positioning device to the bone plate. The method may include attaching the soft tissue elevator by attaching a second abutment of a second curved portion of the positioning device to the soft tissue elevator. The first and second abutments may have a first diameter and the first and second curved portions may have a second diameter different from the first diameter. The second diameter may be less than the first diameter. The method may include detaching the positioning device from the bone plate. The first and second incisions may be positioned spaced apart on a bone. The step of moving the soft tissue elevator may separate and lift soft tissue away from the bone. During the step of pulling the bone plate, the first abutment of the positioning device may engage a surface of the bone plate to secure the positioning device to the plate. The positioning device may be substantially rigid. The bone may be, for example, a femur bone, tibia, or bones of the skull, etc.

Another aspect of the present disclosure is a method of positioning an implant, such as a bone plate, on a bone. The method includes attaching a first end of a positioning device to a soft tissue elevator, attaching a second end of the positioning device to a bone plate, and pulling the soft tissue elevator, thereby pulling the positioning device and the bone plate.

DETAILED DESCRIPTION

As used herein, the term "proximal" refers to a location closer to an individual's heart, and the term "distal" refers to a location farther away from the individual's heart. When used in the context of an implant, the terms "proximal" and "distal" refer to locations on the implant closer to, or farther away from, the heart when the implant is implanted in an intended manner.

The present disclosure includes devices, systems and methods for positioning an implant, such as a bone plate, on a bone. The devices and methods are particularly advantageous for minimally invasive approaches. The devices and methods can be used in systems with bone plates, such as for example elongated plates, and soft tissue elevators, which, as shown and described are merely illustrative, and not meant to limit the structure of such devices. Of course, it is contemplated to utilize the devices and methods of the present invention with many different procedures in connection with different bones.

Referring to FIGS. 1-6, positioning device 110 according to a first embodiment of the present disclosure is shown. Positioning device 110 is configured to attach at a first end 114 to an implant, such as below-discussed bone plate 300, and to below-discussed soft tissue elevator 200, at the second, opposite end 116. Device 110 includes body 120 extending between first and second ends 114, 116 along a central axis. As shown in the top view of FIG. 3, body 120 is substantially "V" or "U" shaped. In this manner, body 120 includes two arms 125 spaced apart at second end 116 that connect or conjoin at first end 114 to form base 123. At second end 116, each arm 125 is positioned on opposing sides of the central axis of the body, and the arms define an open recess 136 between them. Arms 125 include elongate portion 127 and curved portions 128 that are hook-shaped. Base 123 also includes a curved portion 128.

Figure 1:
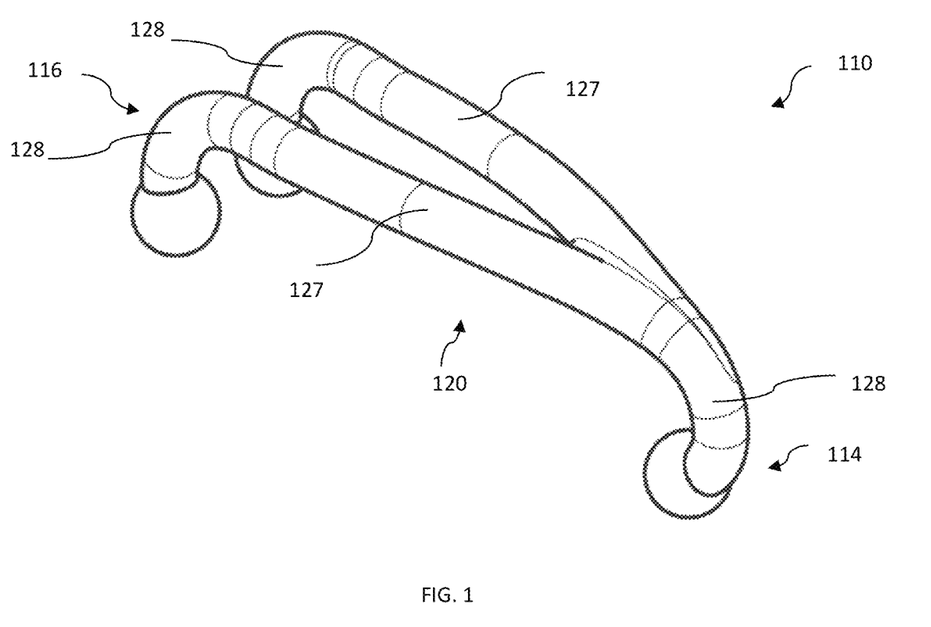
FIG. 1 is a perspective side view of a positioning device according to a first embodiment of the present disclosure.
Figure 2:
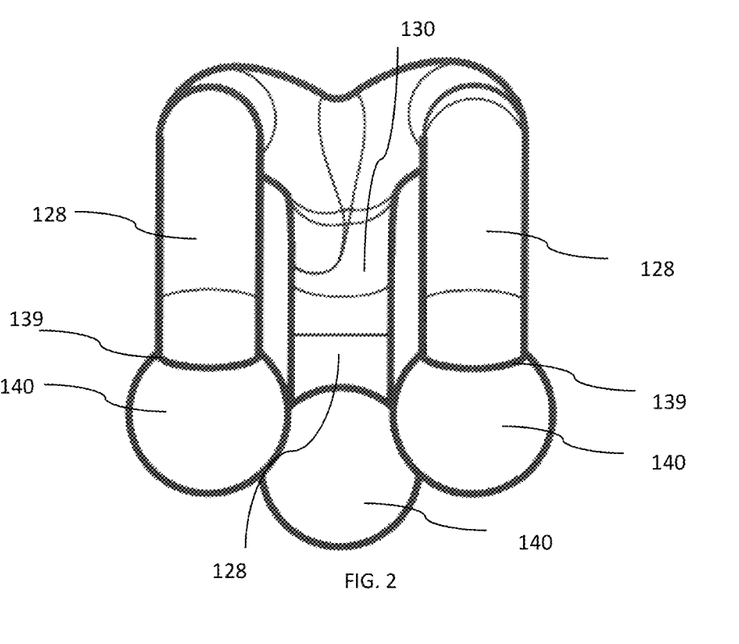
FIG. 2 is a rear view of the device of FIG. 1.
Figure 3:
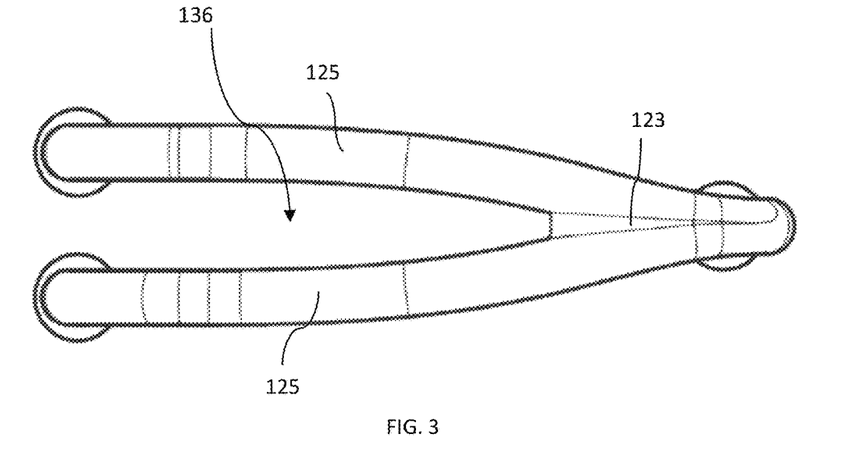
FIG. 3 is a top view of the device of FIG. 1.
Figure 4:
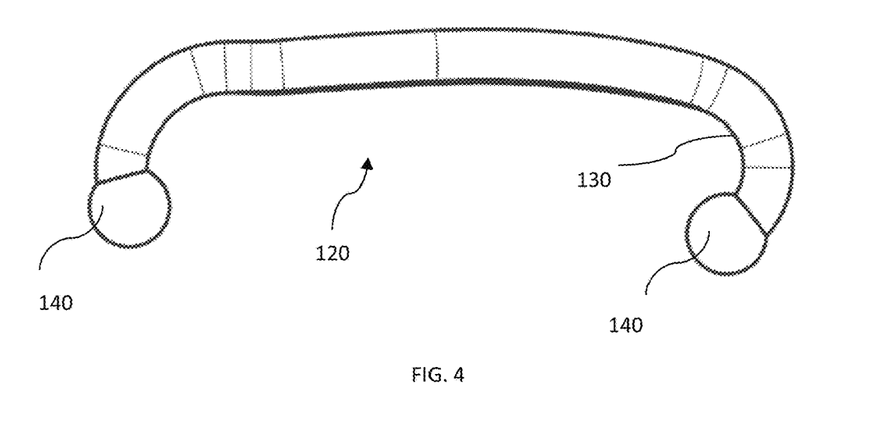
FIG. 4 is a side view of the device of FIG. 1.

Body 120 has a low, curved side profile, which is generally in the shape of an inverted "U" (see FIG. 4) as each of the curved portions extend in the same direction. Arms 125 and base 123 have generally rounded, smooth edges which may result in less soft tissue irritation/damage during a surgery. As shown in FIG. 2 and the side view of FIG. 4, arms 125 and base 123, and in particular curved portions 128, terminate at abutments 140, such that each of the first and second ends 114, 116 has at least one abutment 140. In the illustrated embodiment, first end 114 has one abutment 140, and each arm 125 at second end 116 terminates at an abutment 140, with an abutment edge 139 positioned between curved portion 128 and abutment 140. Abutment 140 has a diameter that is wider than the diameter of each curved portion 128. Although the diameters of both the arms and the abutment are each less than a diameter of at least one hole on a plate, such that the arms and abutment can be inserted within the hole during use. In the illustrated embodiment, abutments 140 are rounded and are shaped to form at least part of a sphere.

Figure 5:
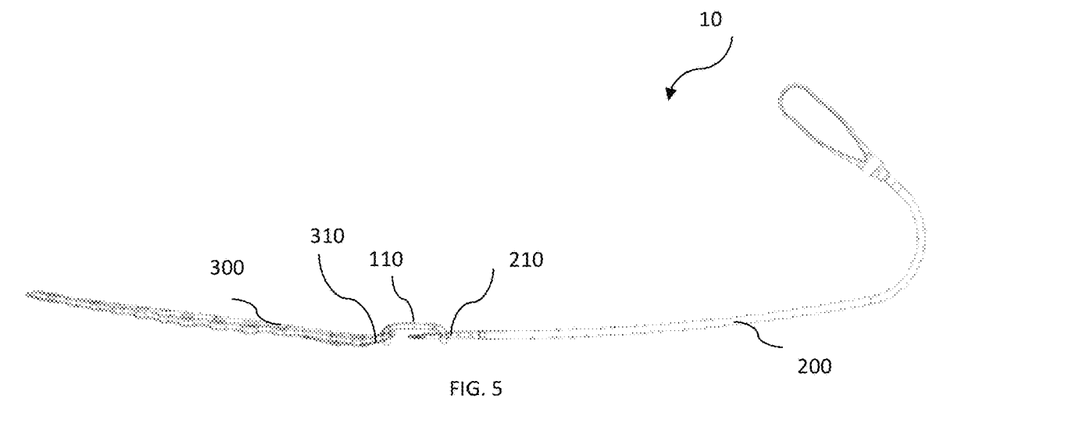
FIG. 5 is a side view of the device of FIG. 1 in conjunction with a bone plate and a soft tissue elevator.
Figure 6:
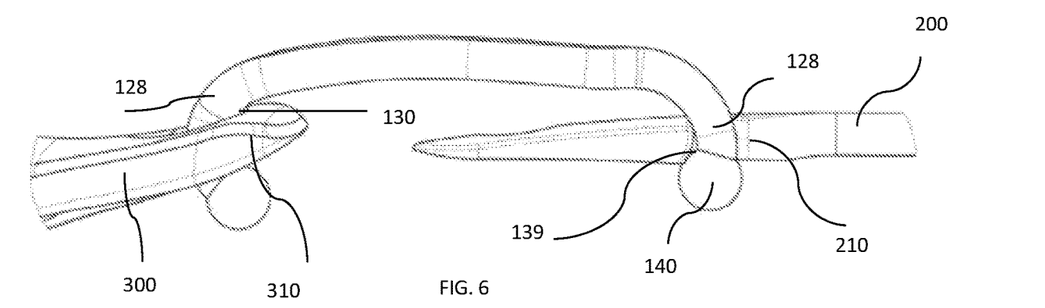
FIG. 6 is an enlarged view of the device, plate, and soft tissue elevator of FIG. 5.

Abutments 140 are designed to abut against respective surfaces of the bone plate and the soft tissue elevator when device 110 is engaged with each of the plate and the elevator as shown in FIGS. 5 and 6. In this manner, device 110 is secured to the plate 300 and to the elevator 200 during movement of the entire construct within the patient's body. As shown, abutments 140 and a portion of the arms 125 and a portion of base 123 are inserted within respective openings of the elevator 200 and the plate 300. Abutments 140 abut against a respective surface of the plate and elevator to secure the curved portions 128 within the opening.

The rounded abutments may reduce irritation to the soft tissue during movement of the positioning device within the body, although, in other examples, the abutments can have any shape, such as trapezoidal, rectangular, polygonal, etc.

Positioning device 110 may be monolithic and may be formed layer-by-layer using an additive layer manufacturing (ALM), i.e., 3D printing, process so no separate connection mechanism is necessary to bring together any of the components of the device. Alternatively, body 120 may be manufactured as a separate piece from abutments 140, which are subsequently assembled together, such as by welding.

With reference to FIGS. 5 and 6, system 10 includes device 110, soft tissue elevator 200 and bone plate 300. The device is attached at second end 116 to the elevator and attached at first end 114 to the bone plate. The curved portions 128 of the device 110 are sized and shaped to prevent the plate 300 from moving onto the elongated portion of the arms 125. An inner surface 130 of curved portion 128 at first end 114 forms a blocking surface to prevent upward movement of the proximal tip 310 of the plate, as best shown in FIG. 6.

Device 110 may be formed as a single, integral piece formed from any material, including but not limited to metals, such as stainless steel, titanium and its alloys, etc., polymers, or any other suitable materials. Alternatively, arms 125 may be formed from a first material and the abutments formed from a second material different from the first. Regardless of the material used, the device may be substantially rigid. It is also contemplated to include features that enhance or otherwise improve the attachment of device 110 to different plates and elevators. For instance, it is contemplated to roughen, knurl or even magnetize certain portions of device 110 to improve the overall construct.

Figure 7:
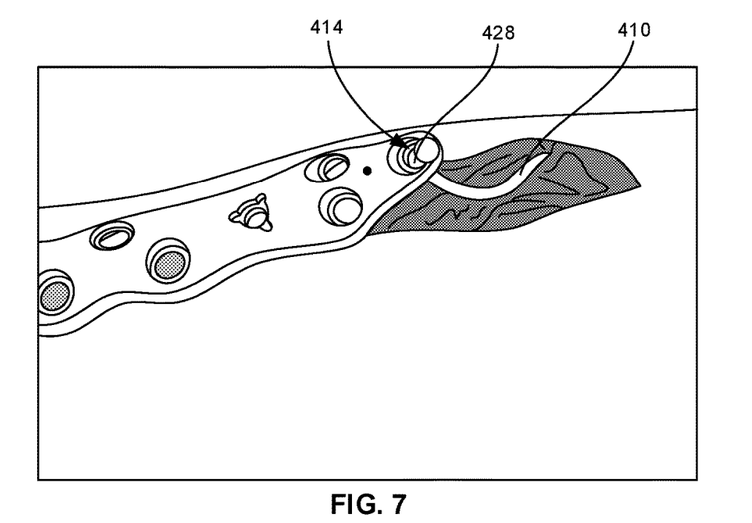
FIG. 7 is a schematic view of a positioning device at least partially within an incision of a leg according to a second embodiment of the present disclosure.
Figure 8:
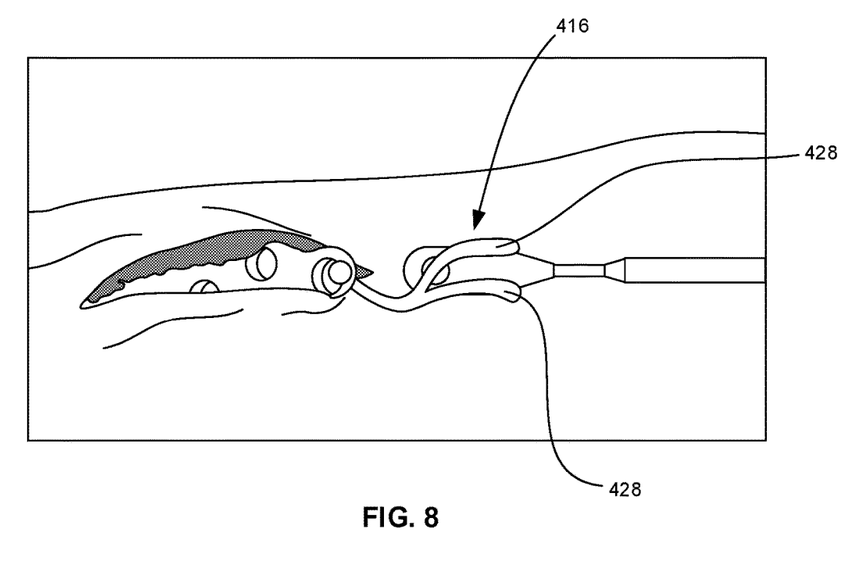
FIG. 8 is a schematic view of the positioning device of FIG. 7 in conjunction with a bone plate and a soft tissue elevator, the plate positioned at least partially within the leg.

FIGS. 7 and 8 show positioning device 410 according to another embodiment of the present disclosure. Positioning device 410 is similar in many ways to device 110 and functions in the same manner As shown from the side view of FIG. 7, the device 410 has a substantially "S" shape in that the curved portions at each end curved in substantially opposite directions. In the illustrated embodiment, curved portion 428 at first end 414 curve upward away from the bone when in use and the curved portions 428 at second end 416 curved downward toward the bone. In this regard, it is contemplated to provide differently shaped positioning devices in accordance with the present invention based upon the planned uses of such devices or given the shape and/or structure of the plates to be positioned.

Figure 9:
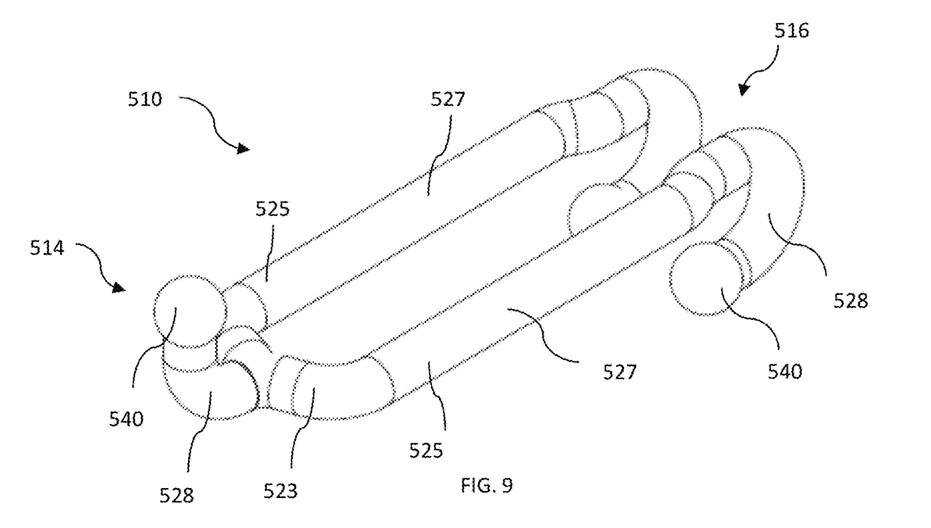
FIG. 9 is a perspective side view of a positioning device according to another embodiment of the present disclosure.

FIGS. 8 and 9 show positioning device 510 according to another embodiment of the present disclosure. Positioning device is substantially similar to positioning device 410. Device 510 includes two arms 525 including elongate portions 527, each elongate portion extends into a curved portion 528 at second end 516. Near first end 514, the elongate sections 527 extend into arcuate sections extending toward a central axis of the device and connect to form an arcuate base 523, which has a curved opened toward second end 516. Curved portion 528 at the first end curves upward, and curved portions 528 at second end 516 curve in an opposite downward direction. Each curved portion terminates in an abutment 540, similar to abutments 140 described above.

Figure 10:
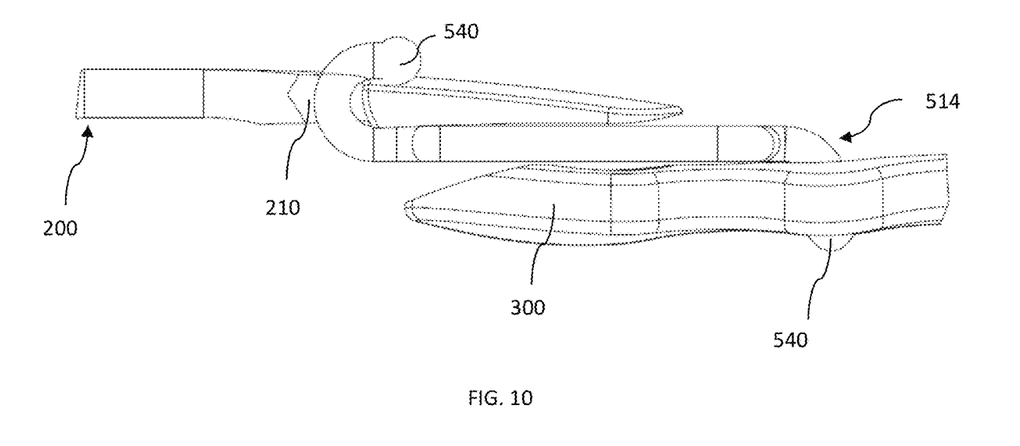
FIG. 10 is a side view of the positioning device of FIG. 9 in conjunction with the bone plate and the soft tissue elevator.

In use as part of a system with bone plate 300 and elevator 200, shown in FIG. 10, first end 514 of the device is positioned within one of the holes of the plate 300. The curved portion 528 of the first end extends from the upper surface of the plate through to the lower surface of the plate, such that abutment 540 engages the lower surface of the plate. The curved portions 528 at second end 516 extend into one or more recesses of the tip 210 of the elevator 200 with abutments 540 engaging a portion of the upper surface of the tip.

Figure 11:
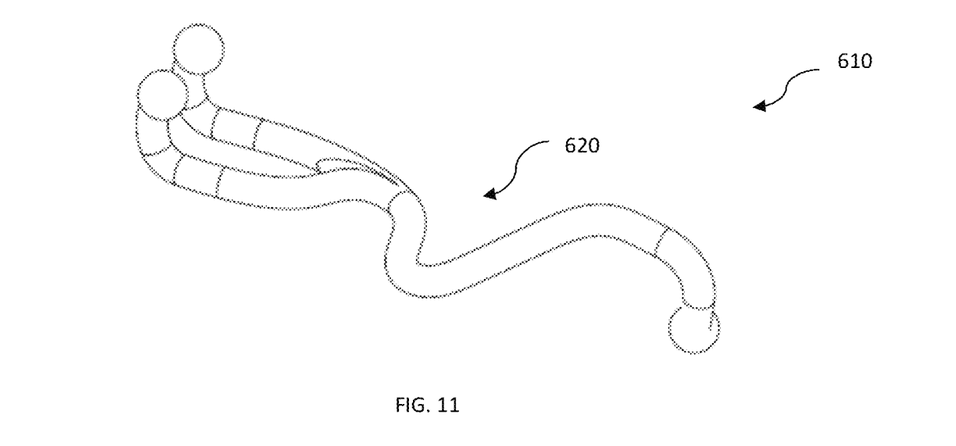
FIG. 11 is a perspective top view of a positioning device according to another embodiment of the present disclosure.
Figure 12:
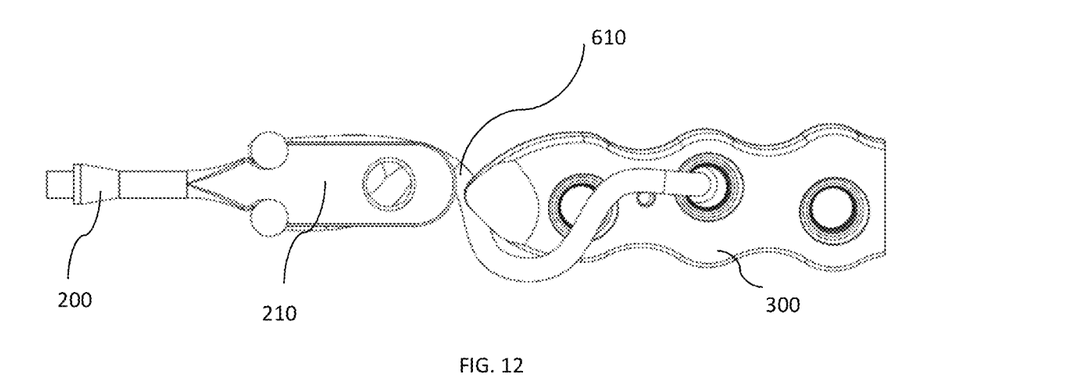
FIG. 12 is a top view of a system including the positioning device of FIG. 11 in conjunction with the bone plate and the soft tissue elevator.
Figure 13:
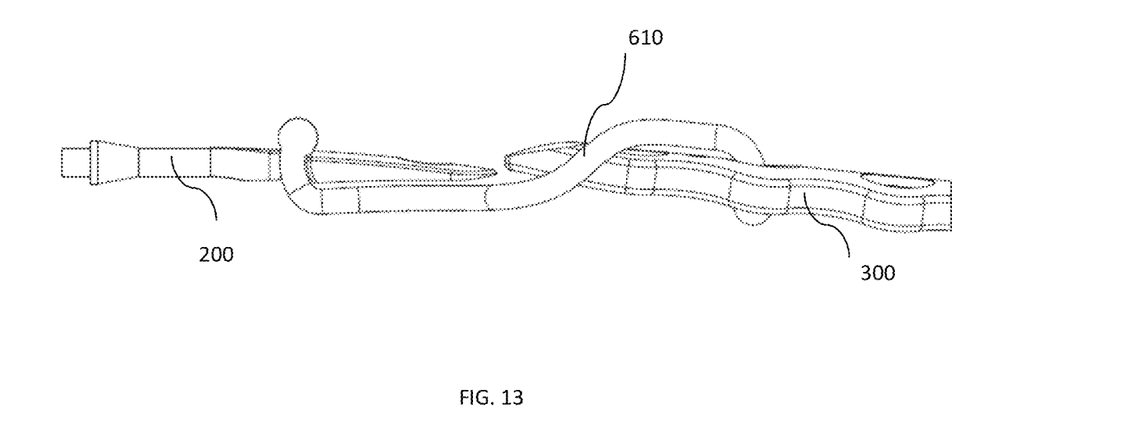
FIG. 13 is a side view of the system of FIG. 12.

FIGS. 11-13 show positioning device 610 according to another embodiment of the present disclosure. Positioning device is similar to the devices 110, 410, and 510 described above, except that body 620 of device 610 does not have elongate portions but instead has a wave shaped body from the top view shown in FIG. 12.

In a method of use of positioning device 110, the surgeon first makes a proximal incision through the skin of a patient over a portion of a bone, such as the femur bone, and then a similar incision distal of the proximal incision. The soft tissue elevator 200 is inserted through the proximal incision and pushed subcutaneously until a tip 210 of the soft tissue elevator reaches the distal incision. As the elevator 200 is pushed along the bone, the tip 210 rides along the bone and separates and elevates tissue away from the bone, creating a canal or path for the bone plate to be inserted and implanted. The use of the soft tissue elevator 200 minimizes soft tissue damage.

At the distal incision, positioning device 110 is attached to tip 210 of the soft tissue elevator 200. In the illustrated embodiment, the arms 125 and abutments 140 at second end 116 are attached to the elevator 200 by positioning them within one or more openings or biased surfaces on the tip 210 of the elevator. The plate 300 is then attached to base 123 at first end 114 of the device 110 and is in position to be pulled through a cleared pathway without having to remove the elevator. In the illustrated embodiment, the abutment 140 and a portion of the base 123 is positioned through a hole on the plate by extending from the upper surface (facing away from the bone) through to the lower surface (facing toward the bone) such that the device is positioned as an inverted "U" shape. In the illustrated embodiment, the arm is positioned through a proximally positioned hole on the plate, and may be through a proximal-most hole of the plate. Although, the plate may be attached to the device 110 prior to the device being attached to the elevator.

Because the device 110 is attached to elevator 200 when the elevator is already in position at the distal incision, and the pathway already cleared for the plate, the method of insertion is simplified and more efficient. This eliminates the need for a surgeon to remove the elevator and thereafter use a dedicated plate inserter to then insert the bone plate.

The surgeon then pulls the soft tissue elevator in the proximal direction toward the proximal incision thereby pulling the positioning device 110 and the plate 300 proximally. The pulling motion also enables engagement between abutments 140 and the surfaces of the plate and the soft tissue elevator to secure the device to each. Additionally, the engagement between the abutment 140 and the plate allows for a stable connection, which reduces undesirable rotation of the plate as it is moved along the bone. The plate is pulled into position, and device 110 is detached from the plate. The elevator 200 and device 110 are removed through the proximal incision. The plate can then be fixed into place.

The pulling motion allows for controlled and precise movement of the plate along the bone, particularly in the case of a pre-contoured plate. The pulling motion eliminates or reduces the tendency of the proximal end of the bone to move away from the bone, such as the case when the plate is pushed rather than pulled. Additionally, the curved portions 128 of the device 110 are sized and shaped to prevent the plate from moving onto the elongated portion of the arms 125. An inner surface 130 of curved portion 128 at first end 114 forms a blocking surface to prevent upward movement of the proximal tip 310 of the plate, as best shown in FIG. 6. Additionally, the curved shape of the device reduces its overall length, which increases the control of the movement of the plate.

Although described with reference to the proximal-distal direction, the method can be employed in any fashion with movements in any direction. Additionally, device 410 can be used in a substantially similar manner, except that the first end 414 of the device may be positioned through a lower surface such that the abutment 440 abuts against the upper surface of the plate.

The present disclosure also includes kits and systems based on the components discussed above. While it is envisioned that these components may be utilized, packaged, sold or designed in any number of systems and kits, representative embodiments will be described below.

The present disclosure can include a kit which can be packaged in a single package as a system or in multiple packages. For example, such a kit may include at least one plate 300, a positioning device 110, and a soft tissue elevator. Any combination of components may be included in a single package or in separate packaging which are later brought together as a kit.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A device for positioning a bone plate comprising:
a body having a first end having a first curved portion and a second end having a second curved portion, each curved portion terminating at an abutment, the first and second ends being part of a single monolithic structure, wherein each abutment has a first diameter and the curved portions have a second diameter less than the first diameter, each abutment facing in the same direction.

2. The device of claim 1, wherein the second end has two second curved portions spaced apart from each other.

3. The device of claim 1, wherein an abutment edge is positioned between each curved portion and each abutment.

4. The device of claim 1, wherein the abutments are shaped as part of a sphere.

5. The device of claim 1, wherein the device is rigid.

6. A system for positioning a bone plate on a bone, the system comprising:
   a soft tissue elevator for clearing soft tissue in a canal of the bone;
   a bone plate; and
   a device for positioning the plate, the device having a first end having a first curved portion and a second end having two second curved portions, the first and second ends being part of a single monolithic structure, the device being attachable at the first end to the bone plate and at the second end to the soft tissue elevator, each end facing in the same direction.

7. The system of claim 6, wherein each curved portion terminates at an abutment.

8. The system of claim 7, wherein the first abutment at the first end is sized and shaped to fit within a hole of the bone plate, and second abutments at the second end are sized and shaped to fit within an opening of the soft tissue elevator.

9. The system of claim 8, wherein the first abutment has a first diameter and the curved portions have a second diameter less than the first diameter.

10. The system of claim 8, wherein the hole of the plate has a third diameter greater than each of the first and second diameters.

11. The system of claim 8, wherein the first curved portion has an inner blocking surface that prevents upward movement of a tip of the bone plate, when the first abutment is positioned within the hole of the plate.

12. The system of claim 6, wherein the two second curved portions of the second end conjoin to form the first curved portion of the first end.

13. A method of positioning a bone plate on a bone, the method comprising:
   inserting a soft tissue elevator into a first incision;
   moving the soft tissue elevator in a first direction along the bone to a second incision;
   attaching a first end of a positioning device to a bone plate by attaching a first abutment of a first curved portion of the positioning device to the bone plate;
   attaching a second end, opposite the first end, of the positioning device to the soft tissue elevator by attaching a second abutment of a second curved portion of the positioning device to the soft tissue elevator; and
   pulling the soft tissue elevator in a second direction, opposite the first direction, such that the positioning device and the bone plate are also pulled in the second direction,
   wherein the first and second ends are part of a single monolithic structure and the first and the second abutments have a first diameter and the curved portions have a second diameter less than the first diameter, each abutment facing in the same direction.

14. The method of claim 13, further comprising the step of detaching the positioning device from the bone plate.

15. The method of claim 13, wherein the first and second incisions are positioned spaced apart on a bone.

16. The method of claim 13, wherein the bone is a femur.

17. The method of claim 13, wherein the step of moving the soft tissue elevator separates and lifts soft tissue away from the bone.

18. The method of claim 13, wherein during the step of pulling, the first abutment of the positioning device engages a surface of the bone plate to secure the positioning device to the plate.

19. The method of claim 13, wherein the positioning device is substantially rigid.

* * * * *